United States Patent
Al-Ali et al.

(10) Patent No.: US 11,559,219 B2
(45) Date of Patent: Jan. 24, 2023

(54) BIO-IMPEDANCE ANALYZER

(71) Applicant: UTI Limited Partnership, Calgary (CA)

(72) Inventors: Abdulwadood Abdullah Al-Ali, Calgary (CA); Brent Maundy, Calgary (CA); Ahmed Elwakil, Sharjah (AE)

(73) Assignee: UTI LIMITED PARTNERSHIP, Calgary (CA)

( * ) Notice: Subject to any disclaimer, the term of this patent is extended or adjusted under 35 U.S.C. 154(b) by 964 days.

(21) Appl. No.: 16/376,603

(22) Filed: Apr. 5, 2019

(65) Prior Publication Data
US 2019/0313935 A1   Oct. 17, 2019

Related U.S. Application Data

(60) Provisional application No. 62/656,088, filed on Apr. 11, 2018.

(51) Int. Cl.
*A61B 5/053* (2021.01)
*G01R 27/30* (2006.01)
*G01R 27/32* (2006.01)

(52) U.S. Cl.
CPC .......... *A61B 5/053* (2013.01); *G01R 27/30* (2013.01); *G01R 27/32* (2013.01)

(58) Field of Classification Search
CPC ..... A61B 5/053; A61B 5/7225; A61B 5/7235; G01R 27/30; G01R 27/32; G01R 27/02
See application file for complete search history.

(56) References Cited

U.S. PATENT DOCUMENTS

| | | | | |
|---|---|---|---|---|
| 6,970,738 | B1 * | 11/2005 | Othman | A61B 5/053 600/547 |
| 10,702,166 | B1 * | 7/2020 | Freeman | A61B 5/0803 |
| 10,737,098 | B2 * | 8/2020 | Perryman | A61N 1/3787 |
| 2015/0061720 | A1 * | 3/2015 | Takano | G01R 31/2642 324/762.01 |

OTHER PUBLICATIONS

Bondarenko, A., et al. "EIS Spectrum Analyser" http://www.abc.chemistry.bsu.by/vi/analyser/. Accessed Jul. 3, 2019.

Maundy, B., et al. "Extracting the parameters of the single-dispersion Cole bioimpedance model using a magnitude-only method" Nov. 2015, 153-157, Comput. Electron. Agric., vol. 119.

(Continued)

*Primary Examiner* — Christopher P McAndrew
*Assistant Examiner* — Zannatul Ferdous
(74) *Attorney, Agent, or Firm* — Brion Raffoul; Arturo Brion (57) ABSTRACT

Systems and methods relating to bio-impedance analysis. The system eliminates the need for hardware phase measurements by using the K-K transform to extract the phase from the magnitude detected. The system has a magnitude detection sub-system that includes a signal generation block, a DC cancellation block, and an amplitude control block. An A/D converter converts the detected magnitude into a digital signal and signal processing is performed to extract the phase of the signal from the magnitude detected.

17 Claims, 10 Drawing Sheets

(56) References Cited

OTHER PUBLICATIONS

Freeborn, T.J., et al. "Extracting the parameters of the double-dispersion Cole bioimpedance model from magnitude response measurements" Jul. 2014, 749-758, Medical & Biological Engineering & Computing, vol. 52.

MacDonald D.D., et al. "Application of Kramers-Kronig Transforms in the Analysis of Electrochemical Systems I. polarization resistance" Oct. 1985, 2316-2319, Journal of the Electrochemical Society, vol. 132.

Urquidi-MacDonald M., et al. "Application of Kramers-Kronig transforms in the analysis of electrochemical systems II. transformations in the complex plane" Oct. 1986, 2018-2024, Journal of the Electrochemical Society, vol. 133.

Kronig, R.D.L. "On the theory of dispersion of X-rays" 1926, 547-557, Journal of the Optical Society of America, vol. 12, No. 6.

King, F.W. "Dispersion relations for some linear optical properties" Hilbert Transforms vol. 2., Apr. 2009, Cambridge University Press.

Urquidi-MacDonald M., et al. "Applications of Kramers-Kronig transforms in the analysis of electrochemical impedance data III. stability and linearity" 1990, pp. 1559-1566, Electrochimica Acta, vol. 35.

Shih, H., et al. "Should the Kramers-Kronig transforms be used for the validation of experimental impedance data" 1989, pp. 325-328, Corrosion Science.

Shih, H., et al. "Concerning the use of the Kramers-Kronig transforms for the validation of impedance data" 1988, pp. 933-938, Corrosion Science vol. 28, No. 9.

Ehm, W., et al. "The evaluation of electrochemical impedance spectra using a modified logarithmic Hilbert transform" Jan. 2000, 145-157, ACHModels in Chemistry, vol. 137.

Tyagal V.A., et al. "Use of the Kramers-Kronig expressions for the analysis of low-frequency impedance" 1972, pp. 54-56, Institute of Semiconductors.

Esteban J.M., et al. "On the application of the Kramers-Kronig relations to evaluate the consistency of electrochemical impedance data" Jan. 1991, 67-76, Journal of the Electrochemical Society, vol. 138.

Bode, H.W. "Relations Between Attenuation and Phase in Feedback Amplifier Design" Jul. 1940, 421-454, Bell Labs Technical Journal, vol. 19.

Bode, H.W., et al. "Network analysis and feedback amplifier design" D. Van Nostrand Company, Inc. 1945.

Al-Ali, A. et al. "Extraction of phase information from magnitude-only bio-impedance measurements using a modified Kramers-Kronig transform" Dec. 2017, 1-16, Circuits, Systems, and Signal Processing.

U. Newton 4th LTD, IAI Impedance Analysis Interface User Manual, 2005.

Mylotta, E., et al. "Supplemental material: BIA device description" Department of Physics, Portland State University, Portland.

Yang, Y., et al. "A Design of Bioimpedance Spectrometer for Early Detection of Pressure Ulcer" Sep. 2005, pp. 6602-6604, Engineering in Medicine and Biology 27th Annual Conference, Shanghai, China.

Analog Devices, AD8302 LF to 2.7 GHz RF IF Gain and Phase Detector, 2002. Rev. A.

Al-Ali, A., et al. "Design and Implementation of a Bio-Impedance Analyzer Based on the Kramers-Kronig Transform" Department of Electrical and Computer Engineering, University of Calgary, Alberta, Canada.

Analog Devices, AD9850 CMOS 125 MHz Complete DDS Synthesizer, 2004, Rev. H.

Chabowski, K., et al. "Simple wide frequency range impedance meter based on AD5933 integrated circuit" Feb. 2015, 13-24, Metrology and Measurement Systems, Mar. 2015.

Newville, M., et al. "Non-Linear Least-Squares Minimization and Curve-Fitting for Python" Nov. 2018, Release 0.9.12.

Kinetis K66 Sub-Family 180 MHz ARM® Cortex®-M4F Microcontroller. Freescale Semiconductor Inc., Jan. 2016.

OPAx355 200-MHz, CMOS Operational Amplifier With Shutdown, Texas instruments, Apr. 2018.

Single 5-Ω SP3T Analog Switch 5-V/3.3-V 3:1 Multiplexer/Demultiplexer, Texas instruments, Aug. 2009.

Bott, A. "Electrochemical Impedance Spectroscopy Using the BAS-Zahner IM6 and IM6e Impedance Analyzers" 1998, p. 54, Current Separations, vol. 17.

Freeborn, T.J., et al. "Electrode location impact on Cole-impedance parameters using magnitude-only measurements" 2016, IEEE 59th Int. Midwest Symposium on Circuits and Systems (MWSCAS).

* cited by examiner

BIO-IMPEDANCE ANALYZER

RELATED APPLICATIONS

This application is a non-provisional patent application which claims the benefit of U.S. Provisional Application No. 62/656,088 filed on Apr. 11, 2018.

TECHNICAL FIELD

The present invention relates to systems for detecting electrical characteristics. More specifically, the present invention relates to systems and methods for use in bio-impedance analysis.

BACKGROUND

At both very low and very high frequencies, phase measurements are highly affected by noise and hardware sampling/delay limitations while magnitude measurements are less affected and are easier to correct using a number of various methods. Examples of in-direct magnitude-only techniques were recently which employ filter transfer functions (known a priori) to construct the phase response from the measured magnitude response. However, these techniques require numerical computation and a priori knowledge of the impedance model of the unknown tissue. These methods have used either a single or double dispersion Cole-Cole impedance model to fit the impedance under test. The equivalent circuit parameters of these models are determined by using measurements from the magnitude response to solve a set of nonlinear equations. Subsequently, having determined the circuit parameters, the phase response of these models can be obtained. Although these models are sufficient for a wide range of bio-impedance measurements, a general phase extraction method which is independent of the impedance fitting model is needed for measurements that do not fit neither the single nor the double dispersion Cole-impedance models.

Years ago, the Hilbert transform pair was proposed as a mathematical tool that can extend an analytic function into the complex frequency domain. These transforms take several forms in continuous time and in discrete time domains. One of the first applications of the Hilbert transform was the study of the relationship between the refractive index and the absorption coefficient in light dispersion where it was shown that they are related to each other by a pair of equations. These equations are now known as the Kramers-Kronig Transform (K-K transform) and can be considered as a new form of the Hilbert transform pair. Later, they were generalized to relate the frequency dependent real part "$R(\omega)$" to the imaginary part "$I(\omega)$" of any transfer function as long as this function is causal, linear, stable and band-limited in the form:

$$I(\omega) = -\left(\frac{2\omega}{\pi}\right)\int_0^\infty \frac{R(x) - R(\omega)}{x^2 - \omega^2}dx \quad (1.1)$$

$$R(\omega) = R(\infty) - \left(\frac{2}{\pi}\right)\int_0^\infty \frac{x \cdot I(x) - \omega \cdot I(\omega)}{x^2 - \omega^2}dx \quad (1.2)$$

There are two conditions for accurate execution of (1.1) and (1.2) namely:

1) The data set should be taken over the range $x_{min}=0$ to $x_{max}=\infty$.

2) The data set should have its points uniformly distributed over the frequency range.

The first condition cannot be satisfied in experimental data leading to what is known as "the tails problem" for systems which have poles or zeros located near the far ends of the frequency measurement points $x_{min}$, $x_{max}$. Truncation of the data can lead to significant errors if there are such critical poles or zeros. Although there was proposed an algorithm to evaluate the K-K transform integrals, tests on this algorithm using real data showed that it had many limitations and restrictions.

Therefore, the transform became employed mainly as a verification tool in commercial impedance measurement software packages, such as Z-Hit, which computes the impedance magnitude from the phase for data quality tests. Using the transform to extract the impedance phase information out of its magnitude information has been reported for low frequency impedance data taken from a chemical reaction. However, not much can be found about their method or its extension for high frequencies as well as other types of data and therefore the K-K transform remained only as a validation tool in the field of impedance measurement. The K-K transform also received some interest in optical analysis where it is sometimes referred to as the Bode relations and is used to obtain the phase angle from the magnitude.

There is therefore a need for systems and methods that, preferably, provide methods that are suitable for bio-impedance analysis. As well, systems that implement these methods are also desirable.

SUMMARY

The present invention provides systems and methods relating to bio-impedance analysis. The system eliminates the need for hardware phase measurements by using the K-K transform to extract the phase from the magnitude detected. The system has a magnitude detection sub-system that includes a signal generation block, a DC cancellation block, and an amplitude control block. An A/D converter converts the detected magnitude into a digital signal and signal processing is performed to extract the phase of the signal from the magnitude detected.

In one aspect, the present invention provides a system for bio-impedance analysis, the system comprising:
- a signal generation block for generating a signal;
- a DC cancellation block coupled to and receiving an output of said signal generation block;
- an amplitude control block receiving an output of said DC cancellation block and coupled between a first probe and said DC cancellation block;
- an analog to digital converter block;
- an operational amplifier circuit coupled between a second probe and said converter block, an inverting input of said operational amplifier being coupled to an output of said operational amplifier by way of a resistor, said converter block also being coupled to said output;

wherein a sample for use in said bio-impedance analysis is to be coupled between said first probe and said second probe; said signal generation block is controlled by at least one processor.

In another aspect, the present invention provides computer readable media having encoded thereon computer readable and computer executable instructions that, when executed, implements a method for calculating phase information for an impedance from a measured magnitude of said impedance, the method comprising:
  a) receiving measured magnitude of said impedance;
  b) performing a data fitting operation to fit
     $\ln(|Z(\omega)|)$ to $\ln(|\hat{Z}(x)|)$
   where $|Z(\omega)|$ is said measured magnitude for said impedance;
  c) dividing a result of step b) into a plurality of segments, each segment being taken over a predefined frequency range;
  d) calculating limits of a numerical integration for each segment, said limits for each segment including $x_{min}$, $x_{max}$, and a step size over N data points;
  e) performing a numerical integration for each point in each segment based on said limits calculated in step d), a result of said numerical integration being said phase of said impedance, said numerical integration being performed on $$\phi(\omega_i) = \left(\frac{2\omega_i}{\pi}\right) \sum_{\underbrace{\omega_{1,k}}_{r}}^{r \cdot \omega_{n,k}} \frac{\ln(|\hat{Z}(x)|) - \ln(|Z(\omega_i)|)}{x^2 - \omega_i^2} \cdot \Delta x_k.$$

In another aspect, the present invention provides a system for bio-impedance analysis, the system comprising:
  a signal generation block for generating an excitation signal;
  at least two signal processing blocks for processing said excitation signal, said at least two signal processing blocks being coupled between a first probe and said signal generation block;
  a magnitude sensing block for detecting a magnitude of an unknown impedance of a sample for use in said bio-impedance analysis, said magnitude sensing block being coupled to a second probe, an output of said magnitude sensing block being a magnitude of said unknown impedance;
  at least one data processing device for determining phase information of said unknown impedance based on said magnitude of said unknown impedance;
  wherein
  said sample for use in said bio-impedance analysis is to be coupled between said first probe and said second probe;
  said signal generation block is controlled by at least one processor.

BRIEF DESCRIPTION OF THE DRAWINGS

The embodiments of the present invention will now be described by reference to the following figures, in which identical reference numerals in different figures indicate identical elements and in which.

DETAILED DESCRIPTION

As noted above, one aspect of the invention involves extracting a signal's phase from its detected magnitude. Continuing from the above explanation, equations (1.1) and (1.2) arise from a linear impedance modeled as $$Z(j\omega) = R(\omega) + j \cdot I(\omega) \qquad (1.3)$$

In order to obtain the phase out of the magnitude we consider the impedance in the following form:

$$Z(j\omega) = |Z(\omega)| e^{j \cdot \phi(\omega)}$$

$$\ln(Z(j\omega)) = \ln(|Z(\omega)|) + j \cdot \phi(\omega) \qquad (1.4)$$

where $|Z(\omega)|$ is the impedance magnitude and $\phi(\omega)$ is its phase angle. Equation (1.1) can therefore be modified to $$\phi(\omega) = \left(\frac{2\omega}{\pi}\right) \int_0^\infty \frac{\ln(|Z(x)|) - \ln(|Z(\omega)|)}{x^2 - \omega^2} dx \qquad (1.5)$$

where $\omega$ is the experimental angular frequency and x is the integration angular frequency.

Figure 1:
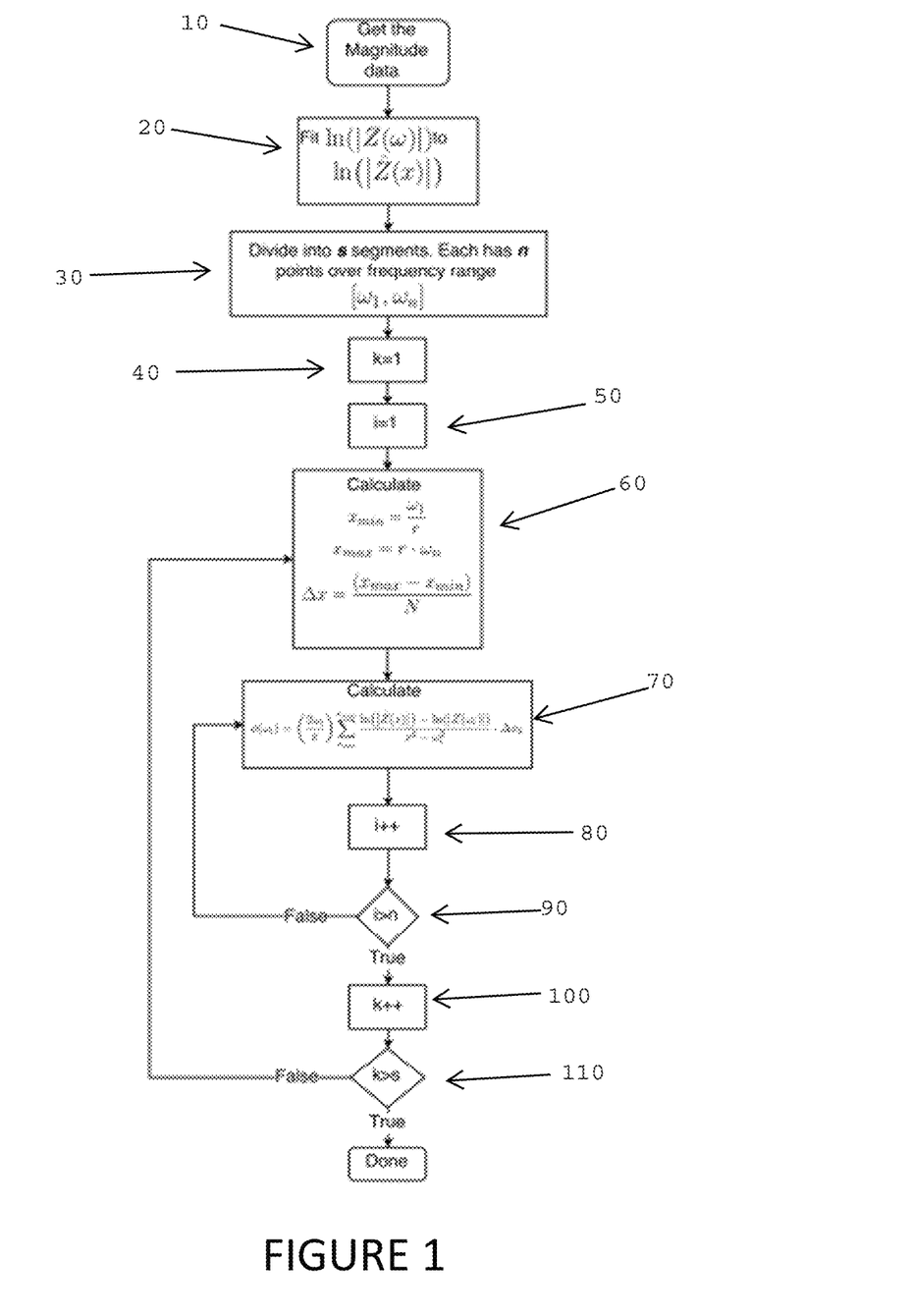
FIG. 1 is a flowchart illustrating the steps in a method according to one aspect of the present invention where a signal's phase is derived from the signal's magnitude.

This integral can be numerically evaluated as $$\phi(\omega) = \left(\frac{2\omega}{\pi}\right) \sum_{x_{min}}^{x_{max}} \frac{\ln(|\hat{Z}(x)|) - \ln(|Z(\omega)|)}{x^2 - \omega^2} \cdot \Delta x \qquad (1.6)$$

where $\hat{Z}(x)$ is the fitted impedance after using linear interpolation. In particular, following the flowchart in FIG. 1 for the integration to be performed, the data should be segmented where each segment is taken over a small frequency range $[\omega_1, \omega_n]$ where n is the number of the points in this segment which can be calculated by Total number of data points/s and then this segment is extrapolated to a wider frequency range where the numerical integration is performed from $x_{min} = \omega_1/r$ to $x_{max} = r \cdot \omega_2$ where r is a scaling factor. This segmenting idea was previously used to obtain a good fitting prior to integration, but it was noted that, to use a polynomial-type fit, each segment should be fitted alone. This process of fitting each segment alone causes the order of the polynomial to be limited by the number of points. In the method of the invention, only linear interpolation is used since it is not affected by the number of points per segment in the log-domain. In one implementation, Matlab's linear interpolation fitting algorithm was used to fit $\ln(|Z(\omega)|)$ to $\ln(|\hat{Z}(x)|)$ and then divide it into s segments. The integration is then evaluated for N points from $x_{min}$ in to $x_{max}$ for each segment with a step $\Delta x = (x_{max} - x_{min})/N$. This modified method which evaluates the integral is given in Equation (1.7) below and requires the right choice of the parameters s, r and N.

$$\phi(\omega_i) = \left(\frac{2\omega_i}{\pi}\right) \sum_{\frac{\omega_{1,k}}{r}}^{r \cdot \omega_{n,k}} \frac{\ln(|\hat{Z}(x)|) - \ln(|Z(\omega_i)|)}{x^2 - \omega_i^2} \cdot \Delta x_k \qquad (1.7)$$

In Equation 1.7, k refers to the specific segment going from 1 to s and i refers to the frequency point being evaluated going from point 1 to n which is the last point in the segment.

The modified K-K method for deriving the phase from the magnitude is illustrated in FIG. 1. The steps in this method are clear from the Figure. The method begins at step 10, that of receiving the magnitude data. Step 20 then fits one function into another function. The result is then divided into s segments with each segment having n points over the frequency range [$\omega_1$, $\omega_n$] (step 30). Steps 40 and 50 initialize the variables k and i with the value of 1. In step 60 a number of values are calculated and in step 70, a more complex function is calculated. Step 80 increments the counter i while step 90 checks if the value for i is greater than the value for n. If i is not greater than n, then the logic loops back to step 70. If i is greater than n, then the logic moves to step 100. In step 100, the value of counter k is incremented while in step 110, the value of k is checked if it is greater than the value of s. If k is less than s, then the logic loops back to step 60. If k is greater than the value of s, then the method ends.

Using a number of simulated datasets, the method illustrated in FIG. 1 was tested. During testing, the "tails problem" was an issue.

The tails problem describes the significant increase in error that may occur at very low or very high frequencies. This problem is significant when the impedance being measured has poles or zeros at those extreme frequencies.

In the method outlined in FIG. 1, the tails problem is reduced by integrating each segment alone on a specific frequency range. Using this approach, only segments close to the end-frequencies are affected in cases when the impedance datasets have critical frequencies close to these end frequencies. Since the location of the critical frequencies of a measured impedance are not known a-priori, this implies that, in any hardware solution, the magnitude data should always be collected over the widest possible frequency range to minimize the likelihood of the tails problem and to ensure that the computed phase is accurate. Alternatively, one can safely assert that the computed phase is accurate over the frequency range that is one decade below the highest scanned frequency and that is one decade above the lowest scanned frequency. That is, if the impedance magnitude was measured over the frequency range (1 Hz-10 MHz) for example, then the tails problem does not affect the calculated phase in the range (10 Hz-1 MHz).

To implement a system that uses the above noted method for use in bio-impedance analysis using simple and inexpensive components, a different design philosophy was needed. Such a portable bio-impedance analyzer with simple hardware can be easily deployed in the field and can be used to conduct continuous measurements. Eliminating the need for the hardware phase measurement by using the K-K transform method to extract the phase from the magnitude reduced the design complexity. In one implementation, the present invention uses a magnitude detection block controlled by a microcontroller. The details of this magnitude detection are shown in FIG. 2A.

Figure 2A:
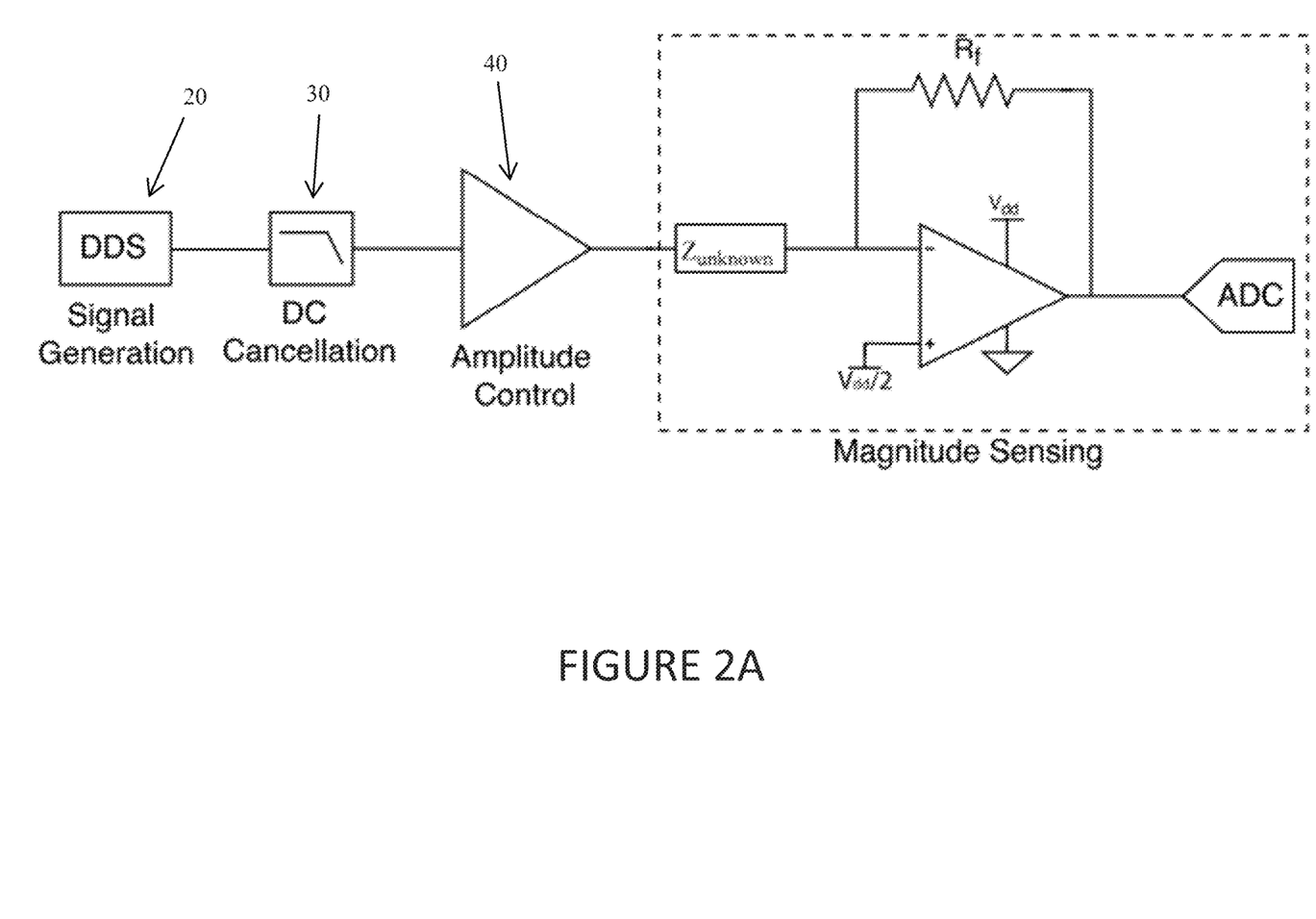
FIG. 2A is a block diagram of a system according to another aspect of the present invention.

FIG. 2A shows a block diagram of one part of the system according to one aspect of the invention. As can be seen, the system 10 includes a signal generation block 20, a DC cancellation block 30, and then an amplitude control block 40. The signal generation block generates a voltage signal (excitation signal) and this generated signal is received by the DC cancellation block 30. The output of this block is then fed to the amplitude control block 40 to control the amplitude of this signal. The magnitude of the signal is measured using the above technique and which is based on a simple gain amplifier.

In one specific implementation, the signal generation block is implemented as a Direct Digital Synthesizer (DDS) to generate an accurate and precise signal.

Figure 3:
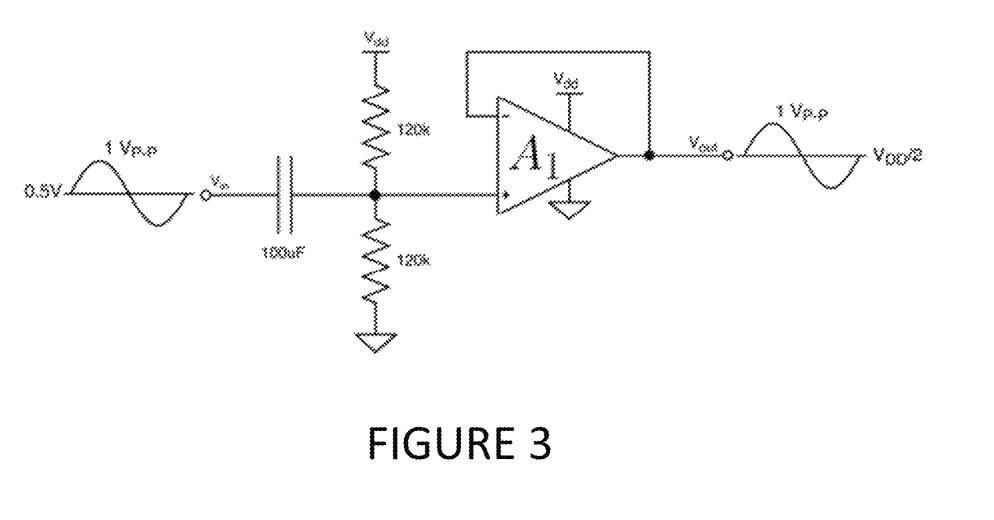
FIG. 3 illustrates a circuit diagram for a DC cancellation circuit for use with the system in FIG. 2A.

Keeping the DC offset constant across the unknown impedance is a crucial issue for some bio-impedance tests since it is necessary to avoid DC polarization at the measured impedance. This could happen when the DC voltage is different on the two ends of $Z_{unknown}$ in FIG. 2A. FIG. 3 shows the DC cancellation schematic. The design of the DC cancellation circuit allows for a high dynamic range for the operational amplifier and the analog to digital converter (ADC). This stage is followed by a buffer to isolate it from the amplification stage.

As can be seen from FIG. 3, the circuit uses an operational amplifier with the inverting input coupled to the op-amp output. A capacitor is coupled between the input voltage and a common node. The between the common node and ground is a first resistor and between the common node and $V_{dd}$ is a second resistor with the same value as the first resistor.

Figure 4:
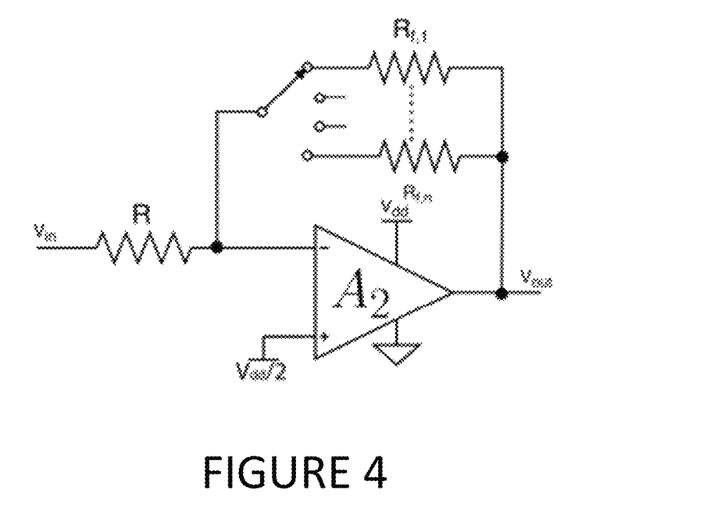
FIG. 4 is a circuit diagram for an amplitude control circuit for use with the system in FIG. 2A.

When conducting bio-impedance measurements of fruits, such fruits are not, generally speaking, sensitive to the excitation signal amplitude. However, in bio-impedance tests such as the ones performed on humans and other biological tissues, these tests require very low excitation voltages to keep such tests safe. Because of this, controlling the amplitude is necessary for any impedance analyzer that needs to work in different applications and in various fields. While programmable gain amplifiers (PGA) can be used to control amplitude, research had shown that such PGA devices were unsuitable to address the system requirements of gain steps while working over the whole frequency range. To this end, a simple non-inverting amplifier with switched feedback resistors was used to control the amplitude of the excitation signal. Such a circuit is illustrated in FIG. 4. In this circuit, the output will have a gain $A_v$ calculated as follows $$A_v = \frac{V_{out_{A1}}}{V_{in_{A1}}} = -\frac{R_{f_1,n}}{R} \qquad (2.1)$$

where n is the number of the feedback resistor and switching between those n resistors can provide any excitation voltage needed.

In the circuit of FIG. 4, the non-inverting input of the operational amplifier is coupled to $V_{dd}/2$. Between the input and a common node is a resistor and the common node is coupled to the inverting input to the op-amp. The common node is also coupled to a selector switch that selects between a number of resistance values, each of which is coupled to the op-amp output.

Figure 5:
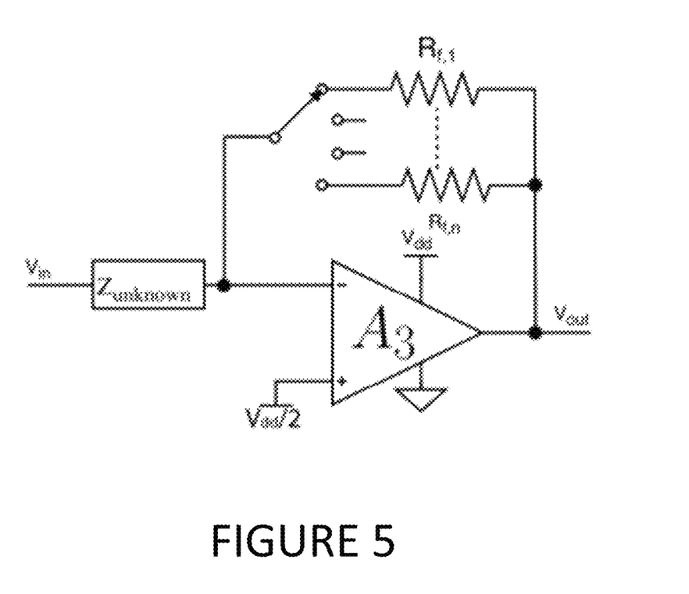
FIG. 5 is a circuit diagram for a magnitude sensing circuit for use with the system illustrated in FIG. 2A.

To understand how the magnitude sensing amplifier works, the basic inverting amplifier circuit shown FIG. 5 is a starting point. This circuit in FIG. 5 is similar to the circuit in FIG. 4 where the non-inverting input to the operational amplifier is coupled to $V_{dd}/2$. The unknown impedance (i.e. the impedance to be measured) is between the input and the common node. The common node is also coupled to the inverting input of the op-amp. As well, the common node is coupled to a switch that selects among a number of resistor values. These resistances are all coupled to the op-amp output.

Analyzing the circuit gives the following well known inverting amplifier gain equation:

$$\left|\frac{V_{out_{A2}}}{V_{in_{A2}}}\right| = \frac{R_{f_2}}{|Z_{unknown}|} \quad (2.2)$$

where $|V_{in_{A2}}|$, is the input signal amplitude to this stage, $|V_{out_{A2}}|$ is the output signal amplitude from this stage, $R_{f_2}$ is the switched feedback resistor and $|Z_{unknown}|$ is the magnitude of the unknown impedance that is being measured. Re-arranging equation (2.2) to solve for $|Z_{unknown}|$ yields, $$|Z_{unknown}| = R_{f_2} \cdot \left|\frac{V_{in_{A2}}}{V_{out_{A2}}}\right| \quad (2.3)$$

While both $R_{f_2}$ and $|V_{in_{A2}}|$ can be controlled by the microcontroller, $|V_{out_{A2}}|$ is the only unknown parameter that needs to be measured to obtain the magnitude of $Z_{unknown}$.

With $|V_{in_{A2}}|$ set to be constant throughout the sweep in most cases, the value of the feedback resistor $R_{f_2}$ is the only value that can be controlled to cover a high impedance range. The choice of the feedback resistor $R_{f_2}$ determines the maximum and minimum unknown impedance that can be measured as follows:

$$|Z_{unknown}|^{max} = R_{f_2} \cdot \left|\frac{V_{in_{A2}}}{V_{out_{A2},min}}\right| \quad (2.4)$$

$$|Z_{unknown}|^{min} = R_{f_2} \cdot \left|\frac{V_{in_{A2}}}{V_{out_{A2},max}}\right| \quad (2.5)$$

In the above equations, $V_{out_{A2},min}$ is the minimum amplitude output voltage that can be read by the ADC and $V_{out_{A2},max}$ is the maximum amplitude voltage which will not saturate both the ADC and the operational amplifier. In one implementation of the invention, the feedback resistor can be automatically switched using the microcontroller to cover any impedance range of interest. This was done by using a switch in the op-amp feedback loop as shown in FIG. 5.

The ADC marks the end of the magnitude detection hardware where the output voltage signal $v_{out_{A2}}$ is digitized to arrive at the amplitude $|V_{out_{A2}}|$. The ADC also controls the frequency range that can be covered using the system. In one implementation, the internal ADC of the microcontroller was used. For this implementation, with a maximum sampling frequency of 500 kHz for the internal ADC, the frequency range would be limited to 100 kHz, since at least 5 points per period are needed to achieve a good fitting for the sampled signal. This was solved by using under-sampling to sample signals over 100 kHz up to 10 MHz. The idea of under-sampling states that one needs to sample the signal with at least double its bandwidth instead of double its maximum frequency, where the bandwidth of the signal can be controlled by the number of cycles being sampled. Using this technique simplified the overall system design. As well, it also reduced the cost since the technique eliminated the need for an external high sampling ADC. Such an external sampling ADC would have required special printed circuit board (PCB) design and a field-programmable gate array (FPGA) for control.

The system is controlled by a microcontroller unit (MCU) which excites the signal through the DDS, sets the values of $R_{f_1}$ and $R_{f_2}$ through the switches and digitizes the output signal. In one implementation, a personal computer utilizing specific program code communicates with the MCU to set the parameters (f, $R_{f_1}$, $R_{f_2}$). Also, the PC reads the digitized signal to process it and then calculate the unknown impedance magnitude $|Z_{unknown}|$ and extract the phase using the K-K transform afterwards.

Figure 2B:
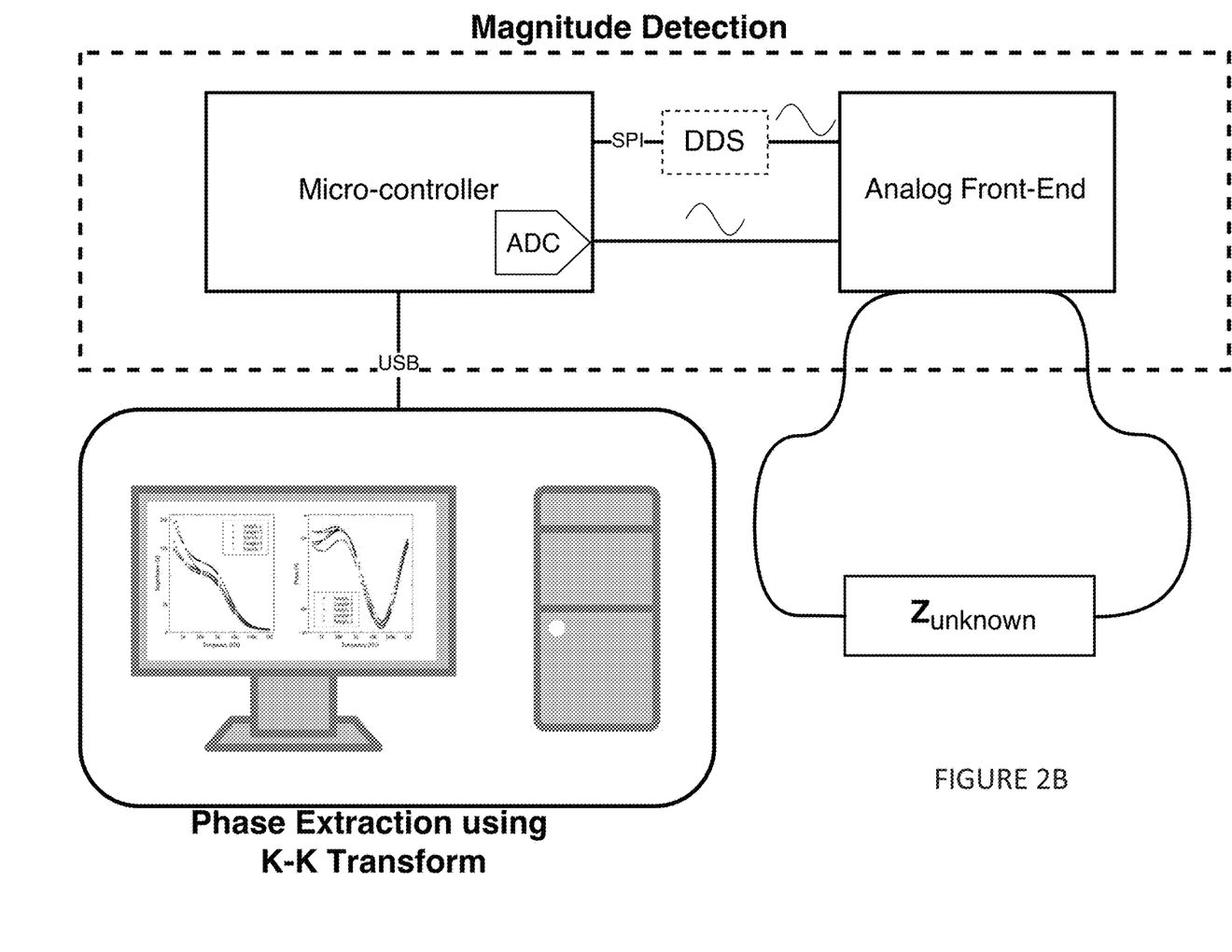
FIG. 2B is a block diagram of a larger system that includes that sub-system in FIG. 2A and the data processing sub-systems that performs the phase extraction from the detected magnitude.

Referring to FIG. 2B, a block diagram of one specific implementation of the present invention is illustrated. As can be seen, the larger system includes the microcontroller (of which the ADC is a part of) that controls the DDS, the front end analog system illustrated in FIG. 2A, and the processor (in this case a PC) that implements the K-K transform to determine the phase information for the impedance.

Figure 6:
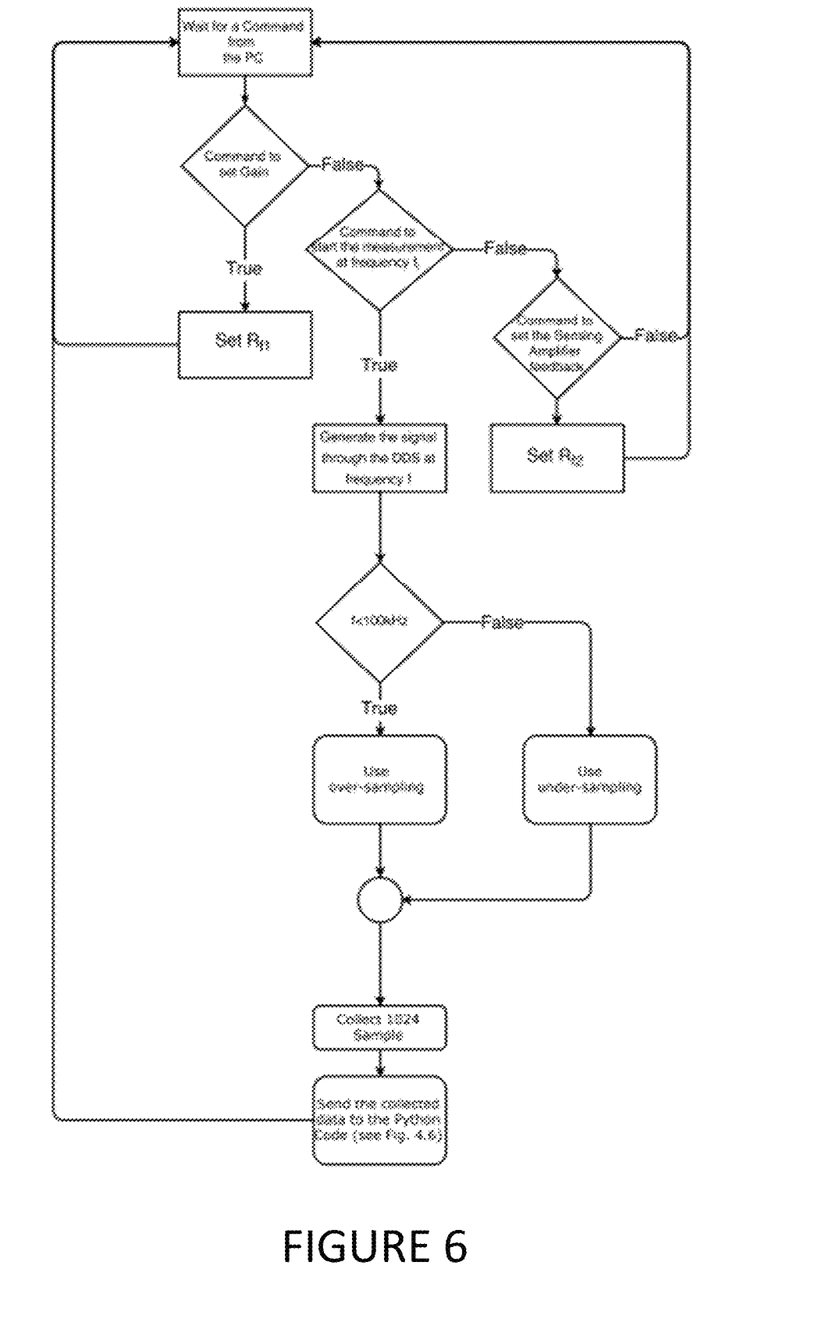
FIG. 6 is a flowchart detailing the steps in a method executed by a microcontroller processor when controlling the system illustrated in FIG. 2A.

Referring to FIG. 6, the flowchart in this figure shows the steps executed by the microcontroller to collect data samples. In brief, the microcontroller starts by receiving a command through the serial port to either set the value of one of the two feedback resistors or to generate the excitation signal at the specified frequency. The microcontroller then decides to either use over-sampling to sample the signals under 100 kHz or use under-sampling to sample signals over 100 kHz and up to 10 MHz and to set the sampling frequency accordingly. This assures that at least one period of the output signal "$V_{out_{A2}}|$ is being sampled. Finally, the microcontroller code collects 1024 samples then sends these samples to the PC where further processing is performed.

Figure 7:
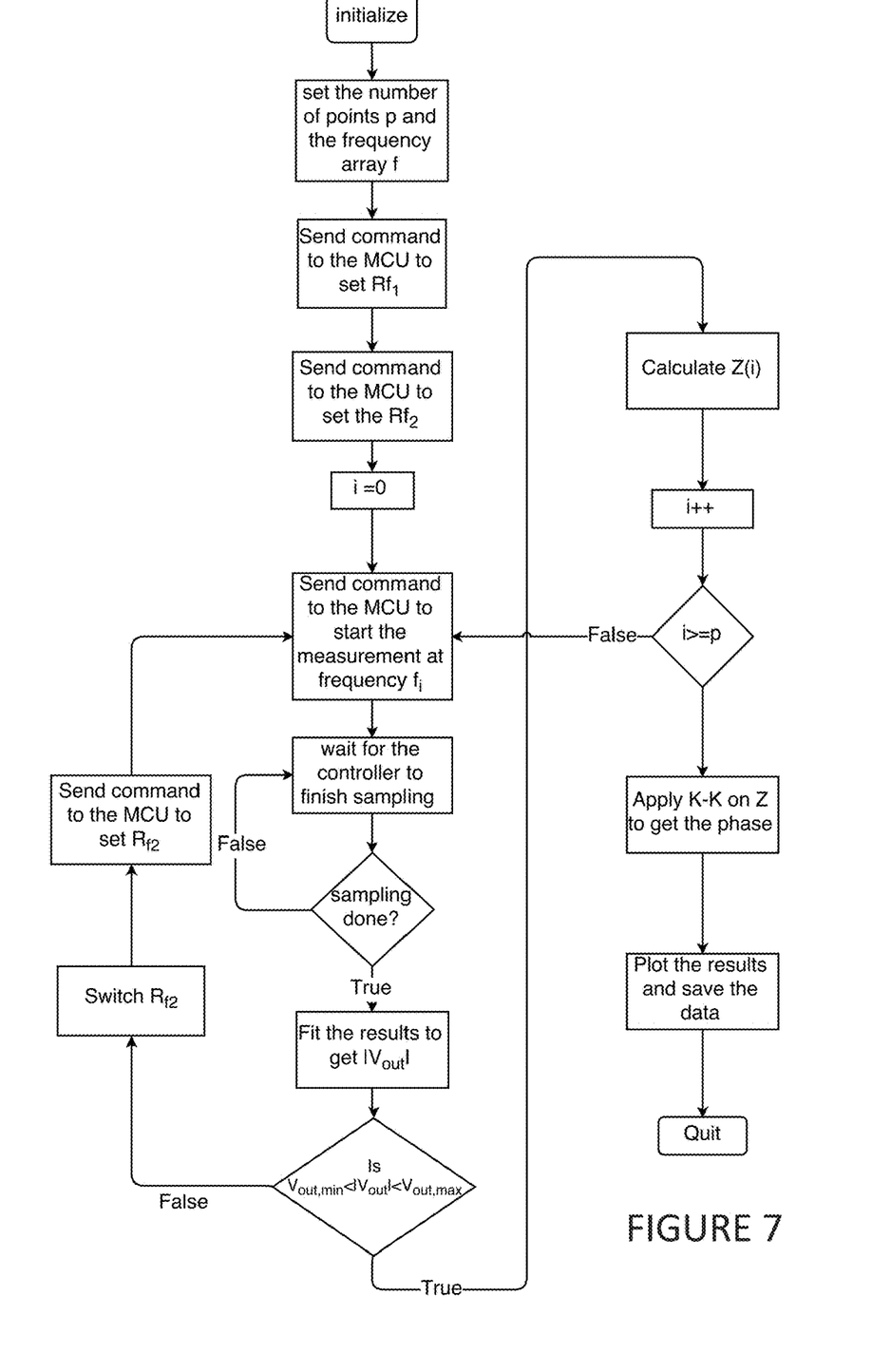
FIG. 7 is a flowchart showing the steps in a method to extract the phase from magnitude readings, the method being executed by another processor after that processor has received the results of the method detailed in FIG. 6.

Once the samples have been received by the PC (or any other suitable processing device), these samples are processed further. The data is processed according to the steps illustrated in FIG. 7. It should be clear that the steps in FIG. 7 detail not only the processing of the data but also controls the frequency sweep. FIG. 7 details the initialization of the sweep by connecting to the microcontroller through the serial interface, and then setting the values of the feedback resistors $R_{f_1}$ and $R_{f_2}$ through the microcontroller to set the gain and the impedance range of operation. Afterwards, the processor executing the steps starts sweeping the frequencies using a predefined frequency array. At each frequency point, according to one implementation, the processor receives the digitized signal from the microcontroller and fits this digitized signal to a sine wave using a suitable fitting algorithm. The digitized signal is fitted to the following equation $$x(t) = A \cdot \sin(f_i \cdot t + \phi) + DC \quad (2.6)$$

where the fitted signal amplitude A represents the output voltage of the sensing amplifier $|V_{out_{A2}}|$.

This value determines whether to switch the value of $R_{f_2}$ and/or calculate the impedance value. During the sweep at each frequency point $f_i$ the fitted data and the extracted magnitude can be shown to the user. After the sweep, the processor applies the K-K transform to the impedance magnitude array to extract the phase of the measured magnitude as discussed above. Finally, in one implementation, the impedance magnitude and phase are plotted for the user to view the results. These plotted results can then be saved into a text file.

Regarding implementation, a number of well-known and readily available components were used to construct one implementation of the system. Regarding the microcontroller, an ARM® CorteX®-M4F Microcontroller was used. This is a fast controller with a clock speed of 180 MHZ and two 16-bit SAR ADCs that can reach a sampling frequency of 500 kHz. In one implementation of the system, the Teensy 3.6 controller board was used. This board has an ARM® Cortex®-M4F in its core. This board was used since it can be programmed using the Arduino integrated development environment (IDE) which is an open source widely used IDE. Also, as discussed above, the AD9850 was selected in one implementation as the signal generator. The module has all the necessary external components and can be easily interfaced with the microcontroller. As well, the module can be simply operated using a 3.3V single supply.

For the operational amplifiers in the system, the OPA3355 package from Texas Instruments was used. This package has three operational amplifiers with high bandwidth and can also be operated with a single 3.3V supply. Switching the feedback resistors was performed using TSSA3357 analog switches from Texas Instruments. One analog switch was used to switch between 3 resistors and two in parallel were used to switch between 6 resistors for $R_{f_1}$ and $R_{f_2}$, respectively. Similar to the other components in the system, these switches can work with a 3.3V power supply. A common power supply improved the portability of the design by making it possible to use an external battery as a power source.

Once the system has been implemented, calibration may be required. For the implementation explained above, calibration was advisable so as to ensure accurate results. The calibration process is performed to account for the non-ideality of the switched resistors. Although the switched resistors are expected to have a linear response with a constant impedance (equal to the resistor value) over the whole frequency range, in practice, it was found that the resistors would cut-off at various frequencies depending on their value and tolerance. However, having a switch in the amplifier feedback causes the non-inverting amplifier to act as an integrator because the switches add parasitic capacitance to the feedback loop. The calibration process is performed using the following equation $$Z_c(f) = \frac{R_c(f)}{\hat{R}_c(f)} \cdot Z(f) \quad (2.7)$$

In the above equation, $Z_C(f)$ is the calibrated impedance, $R_C(f)$ is the actual impedance of the calibration resistor measured using a commercial impedance analyzer, $Z(f)$ is the measured impedance result of equation 2.3 above and $R_c(f)$ is the measured impedance of the calibration resistor RC using the system (the result of equation 2.3 taking $R_c$ as $Z_{unknown}$). The values of $R_c(f)$ show that the resistors are non-ideal as expected and they cut-off at a certain frequency due to this non-linearity. The calibration is usually performed with a resistor value equal to the feedback resistor to calibrate with the amplifier having a gain of 1.

Figure 8:
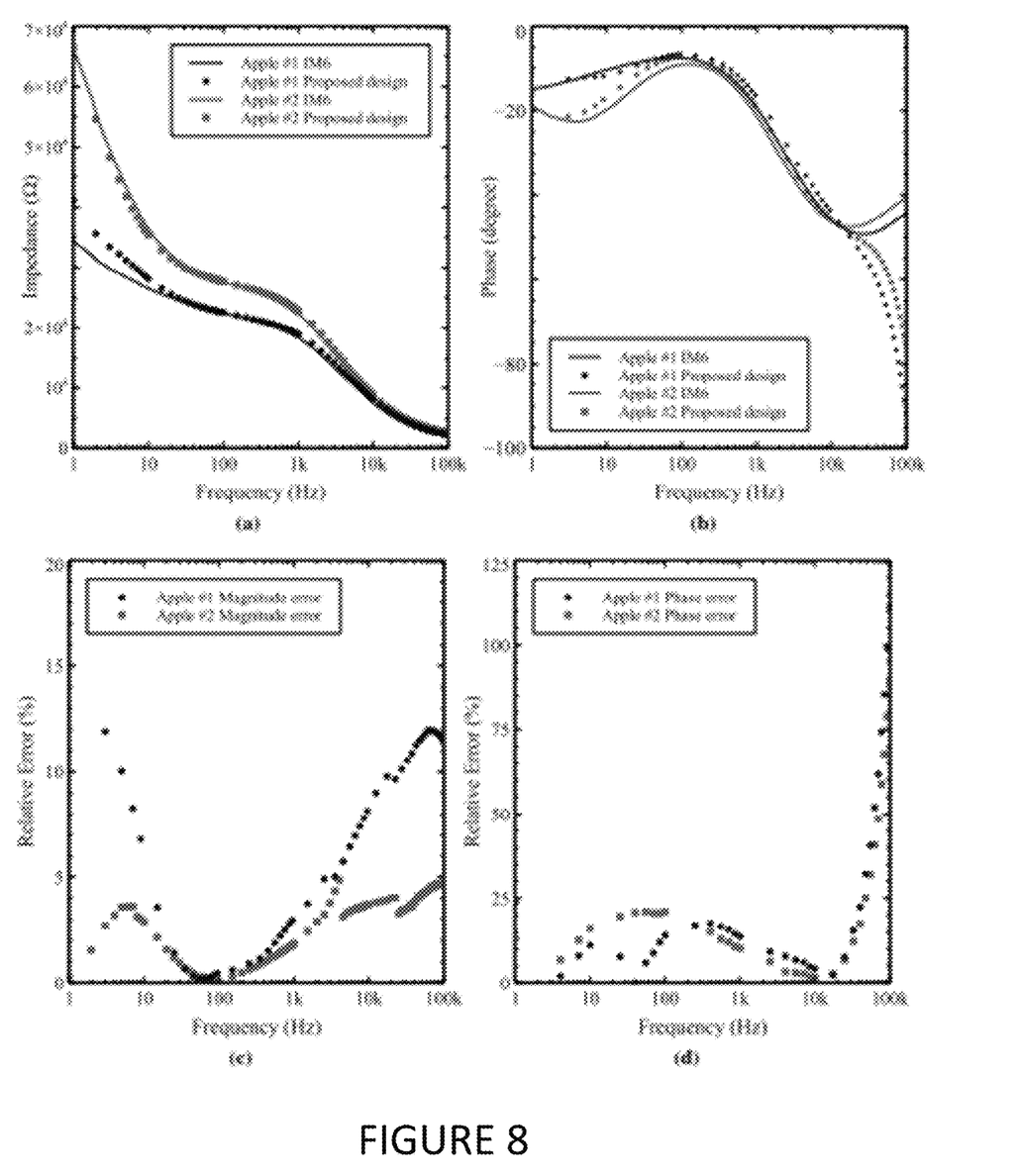
FIGS. 8-10 illustrate test results obtained with commercial equipment compared with one implementation of the present invention.

Results of tests using one implementation of the present invention have been successful. The implementation was tested with two different apples (#1 is a green apple, and #2 is a red apple). They were both tested in the same range but with four feedback resistors (326 kΩ, 120 kΩ, 47 kΩ and 15 kΩ) to cover a wider impedance range. The apples were also measured using a professional impedance analyzer (BAS-Zahner IM6). The results are shown in FIG. 8 and they show good accuracy especially for apple #2 while apple #1 magnitude has some error at the low frequencies. However, both apples have an error in the phase at the edges of the frequency ranges. This is due to the so-called tails problem in the phase extraction algorithm. The tails problem is caused by the existence of poles/zeros below and/or above the covered frequency range. From the results in FIG. 8 it can be seen that there is a pole at frequencies lower than 1 Hz and a zero near 100 kHz which causes the error at those two ends. It should be clear that the upper left figure in FIG. 8 is the impedance magnitude plot while the upper right figure in FIG. 8 is the impedance phase plot. The lower left figure in FIG. 8 is the magnitude error plot while the lower right figure in FIG. 8 is the phase error plot.

Figure 9:
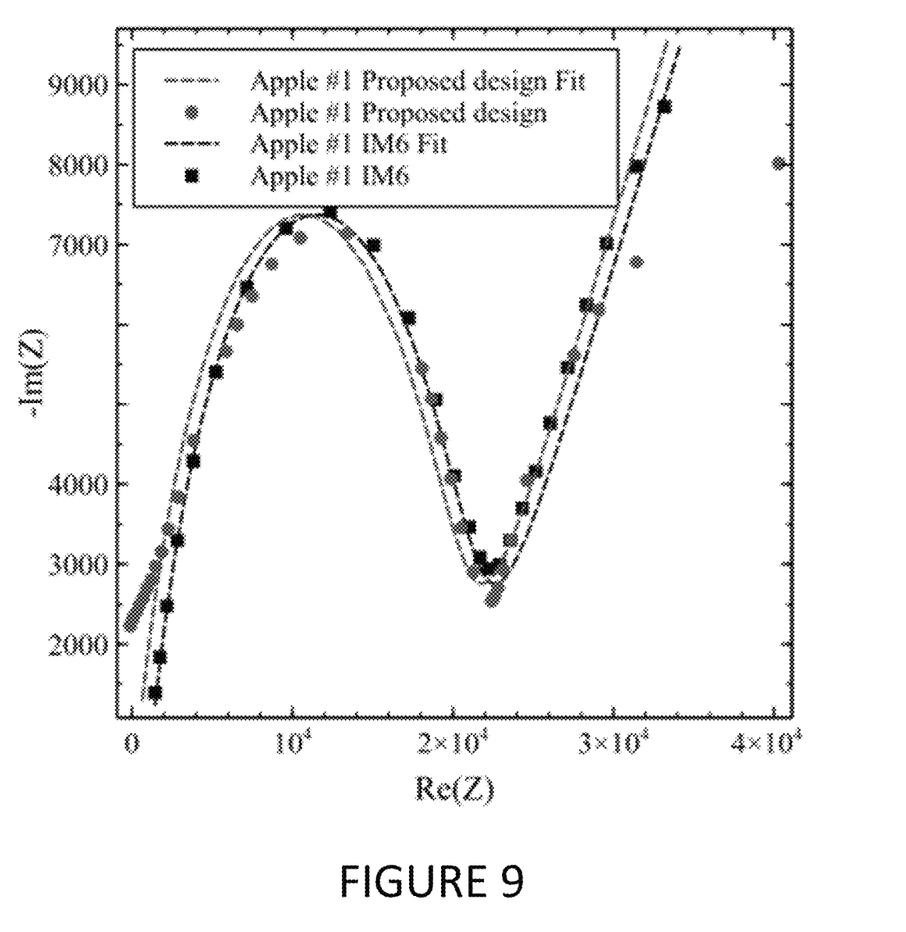
Figure 10:
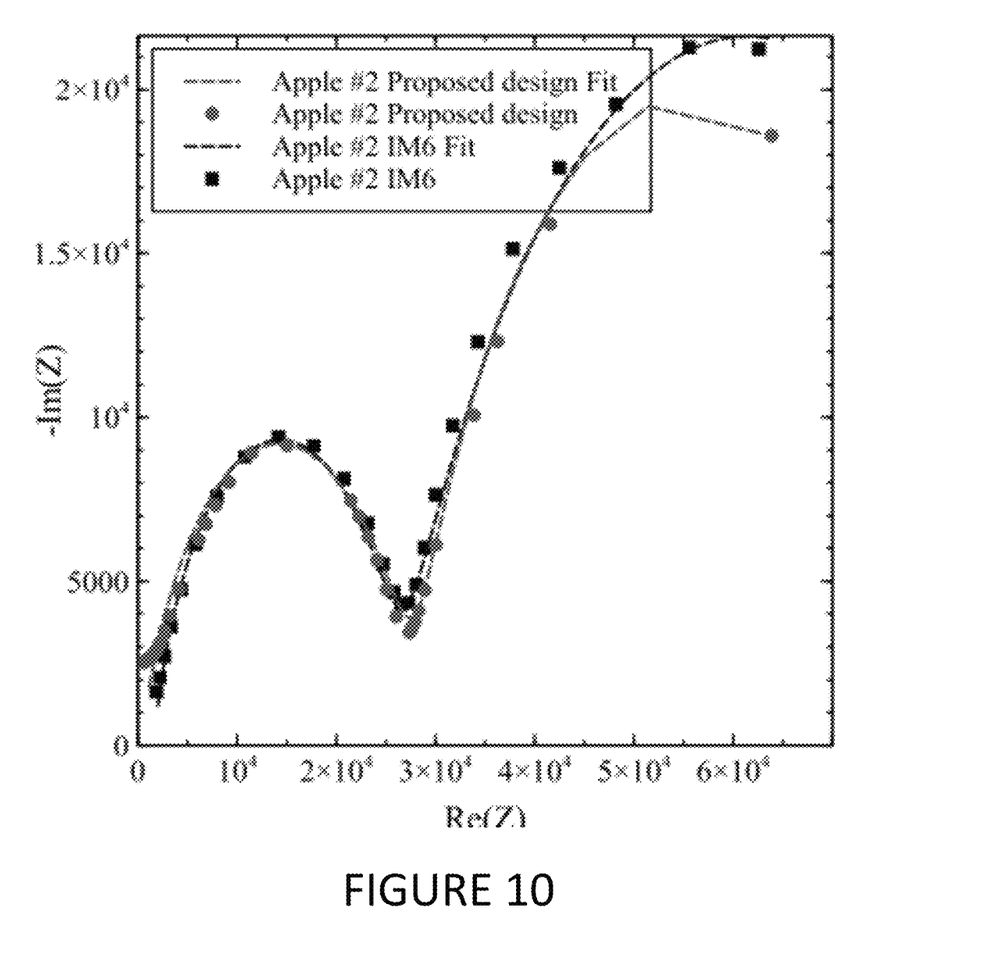

To validate that the measurements are meaningful despite the error in phase, the free EIS software package was used to fit the data from both the implementation of the present invention and the IM6 impedance analyzer to the double-dispersion Cole-Cole model. The Nyquist plots for apple #1 and #2 are shown in FIG. 9 and FIG. 10, respectively. As can be seen, the implementation of the present invention gives close parameters values to those obtained by the professional device (BAS-Zahner IM6).

The embodiments of the invention may be executed by a computer processor or similar device programmed in the manner of method steps, or may be executed by an electronic system which is provided with means for executing these steps. Similarly, an electronic memory means such as computer diskettes, CD-ROMs, Random Access Memory (RAM), Read Only Memory (ROM) or similar computer software storage media known in the art, may be pro-grammed to execute such method steps. As well, electronic signals representing these method steps may also be transmitted via a communication network.

Embodiments of the invention may be implemented in any conventional computer programming language. For example, preferred embodiments may be implemented in a procedural programming language (e.g."C") or an object-oriented language (e.g."C++", "java", "PHP", "PYTHON" or "C#"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink-wrapped software), preloaded with a computer system (e.g., on system ROM or fixed disk), or distributed from a server over a network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

What is claimed is:

1. A system comprising:
a signal generation block for generating an excitation signal;
at least two signal processing blocks for processing said excitation signal, said at least two signal processing blocks being coupled between a first probe and said signal generation block;
a magnitude sensing block for detecting a magnitude of an unknown impedance of a biological sample for use in a bio-impedance analysis, said magnitude sensing block being coupled to a second probe, an output of said magnitude sensing block being a magnitude of said unknown impedance; and
at least one data processing device for determining phase information of said unknown impedance based on said magnitude of said unknown impedance;
wherein
said biological sample for use in said bio-impedance analysis is to be coupled between said first probe and said second probe;
said biological sample is one of: human tissue and other biological tissue; and
said signal generation block is controlled by at least one processor.

2. The system according to claim 1, wherein said magnitude sensing block comprises:
an analog to digital converter (ADC);
an operational amplifier circuit coupled between said second probe and said ADC, an inverting input of said operational amplifier being coupled to an output of said operational amplifier by way of a resistor, said ADC producing a digital version of said output of said magnitude sensing block, and said ADC being coupled to an output of said operational amplifier.

3. The system according to claim 1, wherein said at least two signal processing blocks comprises:
a DC cancellation block for maintaining a DC offset in said excitation signal, said DC cancellation block being coupled to and receiving an output of said signal generation block;
an amplitude control block for controlling an amplitude of said excitation signal, said amplitude control block receiving an output of said DC cancellation block and being coupled between said first probe and said DC cancellation block.

4. The system according to claim 3, wherein said DC cancellation block comprises:
an operational amplifier with an inverting input coupled to an output of said operational amplifier;
a capacitor coupled between an input voltage and a common node;
a first resistor coupled between said common node and ground;
a second resistor coupled between said common node and $V_{dd}$;
wherein said first resistor has a same value as said second resistor.

5. The system according to claim 3, wherein said amplitude control block comprises:
an operational amplifier having a non-inverting input coupled to $V_{dd}/2$;
a resistor coupled between an input to said block and a common node;
a selector switch coupled between said common node and a plurality of resistors;
wherein
said common node is coupled to an inverting input of said operational amplifier;
each one of said plurality of resistors is coupled to an output of said operational amplifier;
said switch couples said common node to one of said plurality of resistors.

6. The system according to claim 2, wherein said resistor in said operational amplifier circuit is a selected resistor that is one of a plurality of resistors, each of said plurality of resistors having a different value from other ones of said plurality of resistors, a value of said selected resistor determining a range of a measured value for said unknown impedance and each of said plurality of resistors being coupled to an output of said operational amplifier.

7. The system according to claim 6, wherein said selected resistor is selected by a switch coupled between said second probe and said plurality of resistors, a position of said switch determining which of said plurality of resistors comprises said selected resistor.

8. The system according to claim 2, wherein said analog to digital converter oversamples a signal from said operational amplifier circuit for signals under 100 kHz.

9. The system according to claim 2, wherein said analog to digital converter undersamples a signal from said operational amplifier circuit for signals at frequencies of between 100 kHz and 10 MHz.

10. The system according to claim 1, wherein said at least one processor comprises a microcontroller.

11. The system according to claim 1, wherein said at least one data processing device determines said phase information of said unknown impedance from said magnitude of said unknown impedance using a method comprising:
a) receiving at said data processing device said magnitude of said unknown impedance;
b) using said data processing device to perform a data fitting operation to fit $$\ln(|Z(\omega)|) \text{ to } \ln(|\hat{Z}(x)|)$$

where $|Z(\omega)|$ is said magnitude for said unknown impedance;
c) using said data processing device to divide a result of step b) into a plurality of segments, each segment being taken over a predefined frequency range;
d) determining, using said data processing device, limits of a numerical integration for each segment, said limits for each segment including $x_{min}$, $x_{max}$, and a step size over N data points;
e) using said data processing device to perform a numerical integration for each point in each segment based on said limits calculated in step d), a result of said numerical integration being said phase of said unknown impedance, said numerical integration being performed on $$\phi(\omega_i) = \left(\frac{2\omega_i}{\pi}\right) \sum_{\frac{\omega_{1,k}}{r}}^{r \cdot \omega_{n,k}} \frac{\ln(|\hat{Z}(x)|) - \ln(|Z(\omega_i)|)}{x^2 - \omega_i^2} \cdot \Delta x_k;$$

wherein said unknown impedance is a bio-impedance.

12. Non-transitory computer-readable media having encoded thereon computer-readable and computer-executable instructions that, when executed, implement a method for calculating phase information for an impedance from a measured magnitude of said impedance, the method comprising:
    a) receiving measured magnitude of said impedance;
    b) performing a data fitting operation to fit $\ln(|Z(\omega)|)$ to $\ln(|\hat{Z}(x)|)$ where $|Z(\omega)|$ is said measured magnitude for said impedance;
    c) dividing a result of step b) into a plurality of segments, each segment being taken over a predefined frequency range;
    d) calculating limits of a numerical integration for each segment, said limits for each segment including $x_{min}$, $x_{max}$, and a step size over N data points;
    e) performing a numerical integration for each point in each segment based on said limits calculated in step d), a result of said numerical integration being said phase of said impedance, said numerical integration being performed on $$\phi(\omega_i) = \left(\frac{2\omega_i}{\pi}\right) \sum_{\frac{\omega_{1,k}}{r}}^{r \cdot \omega_{n,k}} \frac{\ln(|\hat{Z}(x)|) - \ln(|Z(\omega_i)|)}{x^2 - \omega_i^2} \cdot \Delta x_k.$$

13. A method for determining phase information for an impedance from a measured magnitude of said impedance, the method comprising:
    a) receiving at a processor a measured magnitude of said impedance;
    b) using said processor to perform a data fitting operation to fit $\ln(|Z(\omega)|)$ to $\ln(|\hat{Z}(x)|)$ where $|Z(\omega)|$ is said measured magnitude for said impedance;
    c) using said processor to divide a result of step b) into a plurality of segments, each segment being taken over a predefined frequency range;
    d) determining, using said processor, limits of a numerical integration for each segment, said limits for each segment including $x_{min}$, $x_{max}$, and a step size over N data points;
    e) using said processor to perform a numerical integration for each point in each segment based on said limits calculated in step d), a result of said numerical integration being said phase of said impedance, said numerical integration being performed on $$\phi(\omega_i) = \left(\frac{2\omega_i}{\pi}\right) \sum_{\frac{\omega_{1,k}}{r}}^{r \cdot \omega_{n,k}} \frac{\ln(|\hat{Z}(x)|) - \ln(|Z(\omega_i)|)}{x^2 - \omega_i^2} \cdot \Delta x_k.$$

14. The method according to claim 13, wherein said measured magnitude is measured by a system comprising:
    a signal generation block for generating an excitation signal;
    a DC cancellation block for maintaining a DC offset, said DC cancellation block being coupled to and receiving an output of said signal generation block;
    an amplitude control block for controlling an amplitude of said excitation signal, said amplitude control block receiving an output of said DC cancellation block and being coupled between a first probe and said DC cancellation block;
    a magnitude sensing block for detecting a magnitude of an unknown impedance of a biological sample, said magnitude sensing block being coupled to a second probe, an output of said magnitude sensing block being a magnitude of said unknown impedance;
    wherein
        said biological sample is to be coupled between said first probe and said second probe;
        said biological sample is one of: human tissue and other biological tissue; and
        said signal generation block is controlled by at least one separate processor.

15. The method according to claim 14, wherein said magnitude sensing block comprises:
    an analog to digital converter (ADC); and
    an operational amplifier circuit coupled between said second probe and said ADC, an inverting input of said operational amplifier being coupled to an output of said operational amplifier by way of a resistor, said ADC producing a digital version of said output of said magnitude sensing block, and said ADC being coupled to an output of said operational amplifier.

16. The method according to claim 15, wherein said resistor in said operational amplifier circuit is a selected resistor that is one of a plurality of resistors, each of said plurality of resistors having a different value from other ones of said plurality of resistors, a value of said selected resistor determining a range of a measured value for said unknown impedance and each of said plurality of resistors being coupled to an output of said operational amplifier.

17. The method according to claim 16, wherein said selected resistor is selected by a switch coupled between said second probe and said plurality of resistors, a position of said switch determining which of said plurality of resistors comprises said selected resistor.

* * * * *